(12) United States Patent
Groh et al.

(10) Patent No.: US 7,212,612 B2
(45) Date of Patent: May 1, 2007

(54) X-RAY DEVICE

(75) Inventors: Burkhard Groh, Chicago, IL (US);
Volker Heer, Gundelsheim (DE);
Mathias Hörnig, Erlangen (DE);
Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/042,861

(22) Filed: Jan. 25, 2005

(65) Prior Publication Data

US 2005/0169432 A1 Aug. 4, 2005

(30) Foreign Application Priority Data

Jan. 29, 2004 (DE) .................. 10 2004 004 630

(51) Int. Cl.
*G21K 1/04* (2006.01)
(52) U.S. Cl. ........................ 378/150; 378/116
(58) Field of Classification Search ............... 378/98.8, 378/115–116, 119–138, 150, 148
See application file for complete search history.

(56) References Cited

U.S. PATENT DOCUMENTS

| 6,181,769 | B1 | 1/2001 | Hoheisel et al. | |
| 6,222,906 | B1* | 4/2001 | Sakaguchi et al. | 378/98.8 |
| 6,243,438 | B1 | 6/2001 | Nahaliel et al. | |
| 2002/0122534 | A1* | 9/2002 | Polkus et al. | 378/205 |
| 2002/0126799 | A1* | 9/2002 | Saladin et al. | 378/152 |
| 2003/0227997 | A1* | 12/2003 | Petrick et al. | 378/98.8 |

FOREIGN PATENT DOCUMENTS

DE   697 23 081 T2   2/1998
EP   0 908 743 A2   4/1999

* cited by examiner

*Primary Examiner*—Edward J. Glick
*Assistant Examiner*—Hoon Song

(57) ABSTRACT

X-ray device with a detector and an adjustable diaphragm for fading-in an examination area, whereby the detector (6) can be controlled and read-out asymmetrically and the diaphragm (8) can be moved asymmetrically.

4 Claims, 3 Drawing Sheets

X-RAY DEVICE

CROSS REFERENCE TO RELATED APPLICATIONS

This application claims priority to the German application No. 10 2004 004 630.1, filed Jan. 29, 2004 which is incorporated by reference herein in its entirety.

FIELD OF INVENTION

The invention relates to an X-ray device, in particular with a C-arm carrier system, with a detector and an adjustable diaphragm for fading-in X-rays onto an examination area.

BACKGROUND OF INVENTION

In modern digital X-ray systems, the size of the detector is selected with regard to the main examinations to be carried out. This is why different detectors are used for cardiological applications, fluoroscopy examinations or vascular applications, said detectors differing in terms of their size. One important criterion in selecting the detector size is the ease of access to the patient during the angulation of the C-arm carrier system on the X-ray device. It is not possible to perform certain examinations using a detector of a different size, since in this case is not possible for sufficiently close access to the patient to be achieved. Since each detector size is only suitable for certain procedures, a manufacturer must develop various sizes of detector and decide if he wants to cover all types of examinations occurring in practice. Although the provision of a wide diversity of products enables numerous requirements to be met by selecting the appropriate detector for the application concerned, it also results in considerable costs increases.

SUMMARY OF INVENTION

An object of the invention is to create an X-ray device with a detector which can be positioned at the side of a patient at a different distance across its detector surface, which expands the application possibilities of a large detector in the sense of an improved patient access. A problem of this type arises in particular with an X-ray device with a C-arm carrier system.

The object is achieved by the claims. Advantageous embodiments are set out in the dependent claims.

The X-ray device according to the invention allows the diaphragm to be adjusted and the detector to be controlled in such a way that only a partial area of the detector close to the patient is exposed to X-rays, and/or that only the partial area close to the patient is read out. One advantage resulting from the partial area reading-out in that the read-out process can be carried out more quickly so that the calculation time can be saved and examinations can be carried out with a higher image frequency. One special advantage results from the patient proximity to the partial area provided according to the invention, in that the same detector can now be used for examinations, whereby said detector has hitherto been too large for use in a known X-ray device.

EP 0 908 743 A2 discloses an asymmetric ally designed X-ray detector, however this X-ray detector can not be electrically controlled asymmetrically, but it is asymmetrical in terms of its structural edge-side design which is adapted to the anatomy of a body region to be examined.

DE 697 23 081 T2 describes an asymmetrical detector which can be read-out and a correspondingly asymmetrically adjustable diaphragm, but this is designed exclusively for use with CT scanners where the problem of inadequate patient access does not arise because of a generic structure of the CT device. The invention described in DE 697 23 081 T2 discloses the ability to flexibly control the signal/noise ratio, the reconstruction time, the resolution in the axial direction and the sensitivity of partial volume artifacts.

According to one embodiment of the invention there is provision for the detector to be controlled such that one half or a quadrant of the detector surface is readout. With known X-ray devices in the prior art, detectors of 18 cm×18 cm in size are used in cardiology for instance, and detectors of 30×40 cm in size for angiography for example. These larger detectors could not be used for cardiology since the readout area exposed to X-rays was symmetrically arranged onto the detector and the readout area could not be applied sufficiently close to the region to be examined due to the unavoidable border area used for reading-out measurement data. In accordance with the invention, the radiated and read-out subarea of the detector can however be freely selected, nevertheless it is also possible for the subarea in the detector level to be moved, if the detector moves towards a patient or touches the patient. It is therefore possible to operate a detector provided initially for angiography without any problems, such that it can also be used for a cardiological examination for example, by means of X-ray exposure and reading-out a subarea close to a patient.

A further advantage results with detectors which comprise a number of a-Si plates. Since an individual plate is completely read-out in each instance, no correction software is required which is otherwise needed to correct the images in the region of the touching edges.

In addition to its asymmetrically controllable detector, the outstanding feature of the X-ray device according to the invention is the asymmetrically moveable diaphragm. The diaphragm is asymmetrically moveable in comparison with other known X-ray devices, thereby allowing the diaphragm and the detector to be controlled in a coordinated manner. If for instance, the detector is controlled such that a partial area is read-out, the diaphragm can be moved so that the faded-in examination area corresponds to this subarea of the detector surface. This design of the diaphragm primarily serves to protect the patient from any unnecessary exposure to radiation.

A particularly safe and reliable diaphragm which can be moved asymmetrically is achieved by means of several individually moveable diaphragm elements. Each diaphragm element can be controlled along at least one axis. It is particularly preferable that the diaphragm of the X-ray device according to the invention comprises two pairs of diaphragm elements arranged opposite to each other. In this embodiment of the invention, the examination area can be restricted by any of the four sides (left, right, above, below) such that practically no restrictions in respect of the size and location of the examination area result.

A further advantage of the X-ray device according to the invention can be seen in that the image area of the detector can be displayed on a monitor by means of a zoom function.

The full functionality of the digital zoom is provided for the asymmetrical image area which can be selected by a doctor, such that the diagnosis c an be facilitated based on the monitor image displayed in real-time.

It is also possible to adjust the diaphragm, in particular a depth diaphragm, symmetrically in respect of the X-ray tube and only to move the detector. In this case, an asymmetrical detector area can be selected, whereby the isocenter of the X-ray tube can simultaneously be maintained. The selection of the desired area is particularly simple and the visualization on the monitor is particularly clear.

BRIEF DESCRIPTION OF THE DRAWINGS

Further advantages and details of the invention are described in more detail on the basis of an exemplary embodiment with reference to the figures. The figures are schematic diagrams in which.

DETAILED DESCRIPTION OF INVENTION

Figure 1:
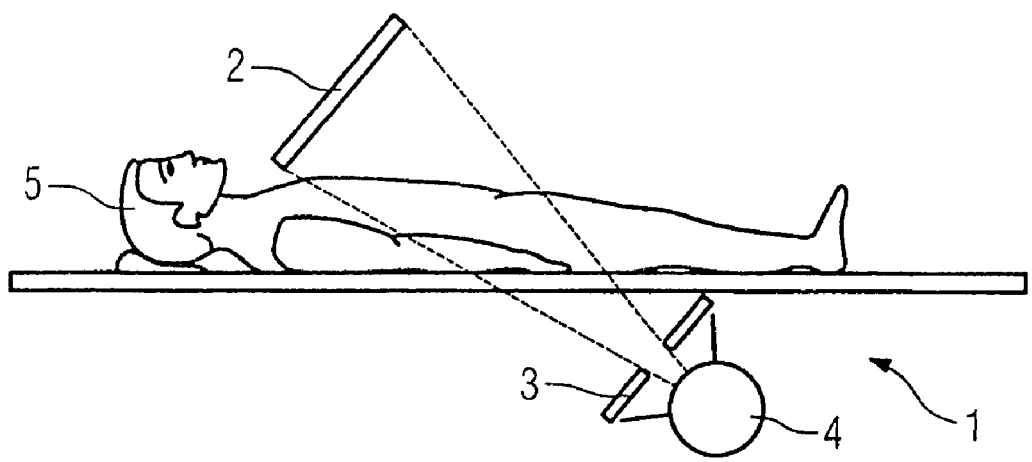
FIG. 1 shows a conventional X-ray device with a detector and an adjustable diaphragm

FIG. 1 shows a conventional X-ray device 1 with a detector 2 and an adjustable diaphragm 3. The diaphragm 3 is located between an X-ray tube 4 and a patient 5 and allows the examination area to be precisely faded-in by symmetrically moving the diaphragm 3.

FIG. 1 shows that with certain examinations the detector 2 cannot be moved sufficiently close to the patient, e.g. cardioangiography, as a result of its size. This is why different size detectors are used in practice. The diaphragm 3 can be moved symmetrically in relation to a detector center point, so that the lateral restrictions of the examination area are equidistant from the center of the detector in each instant.

Figure 2:
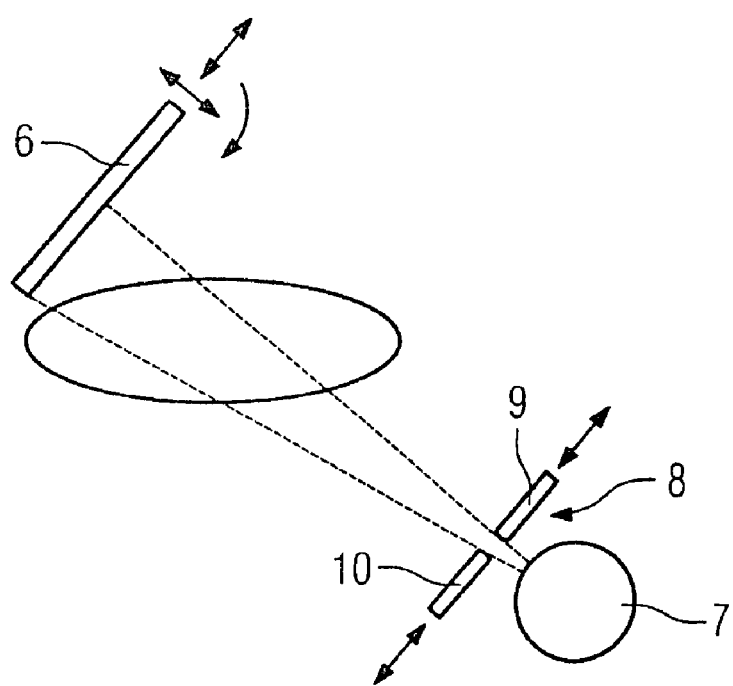
FIG. 2 shows the essential components of an X-ray device according to the invention
Figure 5:
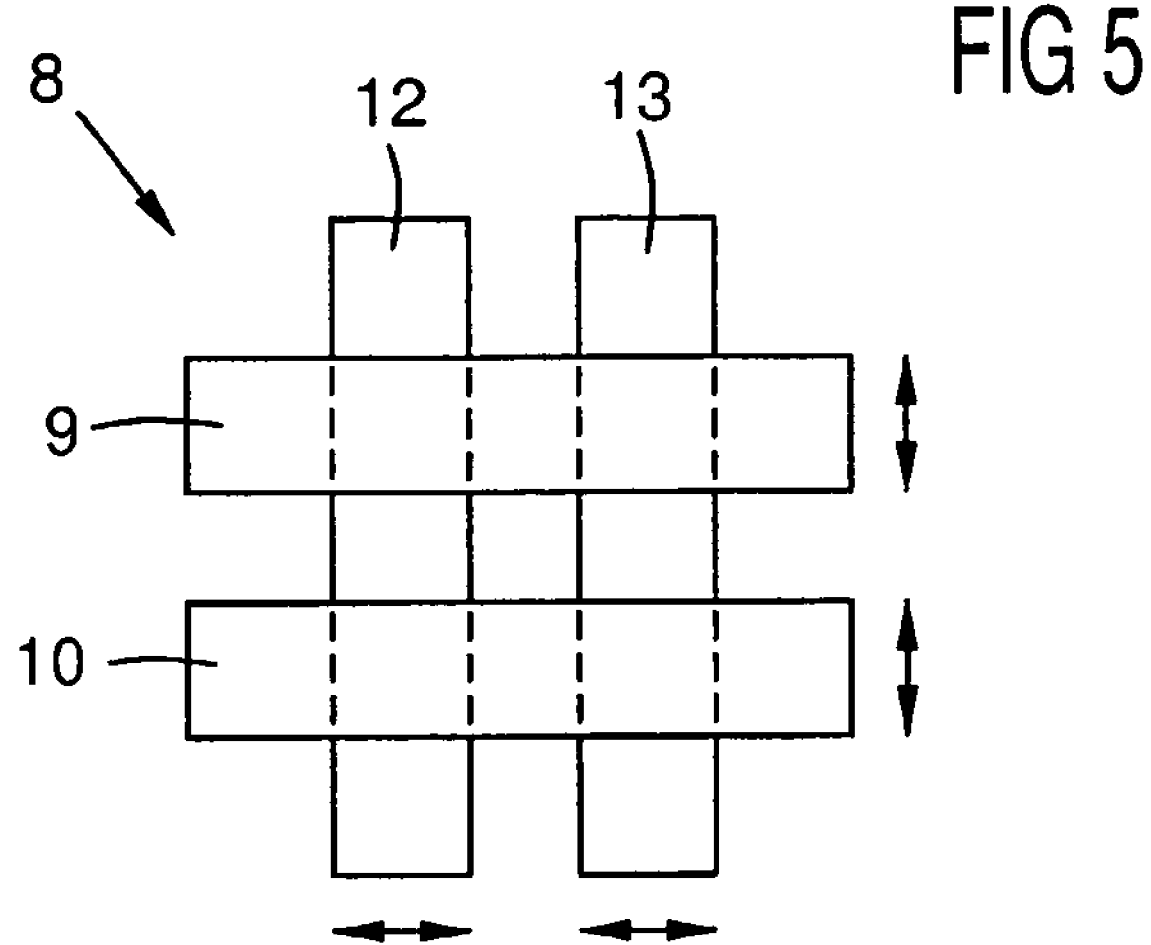
FIG. 5 shows a diaphragm device with four independently movable elements

FIG. 2 shows an exemplary embodiment of the invention, whereby certain components of the X-ray device, which are of no significance for the invention, are not displayed. The detector 6 can be asymmetrically controlled and read out. It is possible to read out only subareas of the detector, so that the calculation speed is correspondingly increased, thus simultaneously allowing a higher image frequency. Detectors are typically read out row by row, on the other hand, the detector 6 has greater flexibility since it allows the reading out of any partial areas. A diaphragm 8 is arranged close to the X-ray tube 7, comprising a pair of diaphragm elements 9, 10 arranged opposite one another. A total of four diaphragm elements are present, which are arranged opposite one another in pairs, whereby both pairs of diaphragm elements lie in parallel planes, so that they can be adjusted independently of one another, without coming into any contact. The second pair of diaphragm elements 12, 13 is shown in FIG 5, which is arranged rotated at 90° opposite to the diaphragm elements 9, 10.

The diaphragm elements 9, 10 can be designed as lead plates, nevertheless it is however also possible to use a flexible material instead of rigid lead plates, for example lead segments which are rolled up onto a drum for space-saving reasons. Each diaphragm element 9, 10 can be controlled and moved separately so that the four delimiting lines of the examination area can be virtually freely selected and adjusted.

In the position shown in FIG. 2, the diaphragm elements 9, 10 are asymmetrically adjusted such that the radiation emitted by the X-ray tube 7 only strikes half of the detector 6. An adjustment of this type is used if a smaller image area is sufficient for the examination to be carried out.

The adjustment of the diaphragm elements 9, 10 and of the second pair (not shown) can be carried out in such a way that any area of the surface of the detector 6 serves as an image area, said image area must thus not necessarily coincide with the edge of the detector 6.

Figure 3A:
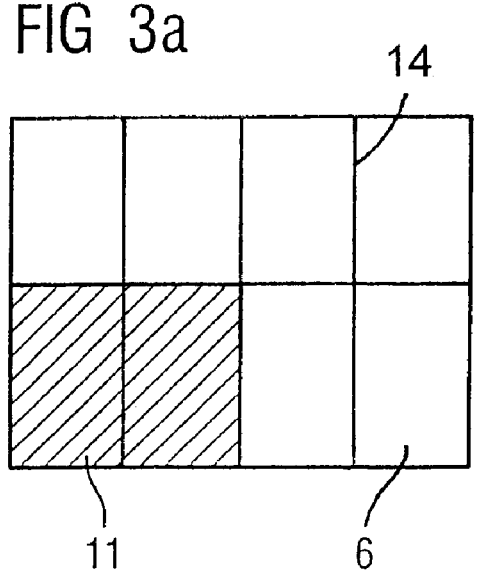
FIGS. 3a and 3b show a detector whereby the image area is moved during the course of an examination
Figure 3B:
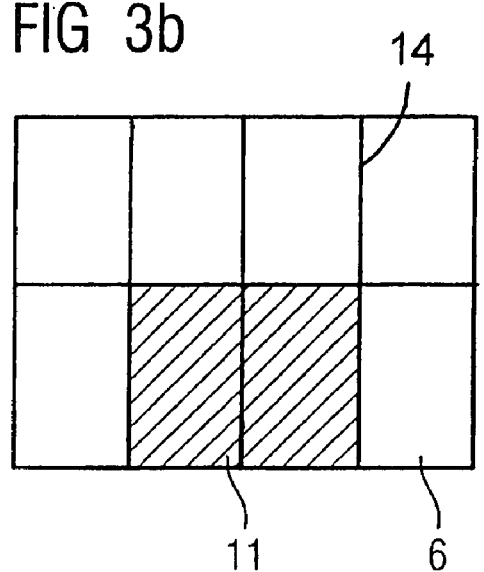

FIGS. 3a–3b show a detector whereby the image area is moved over the course of an examination.

The image area 11 in the left lower corner of the detector 6 is shown in FIG. 3a. This application is then useful if the detector is made up of several individual plates made from aSi plates, since in this case no further correction methods are required for the edge passages.

With an unchanged diaphragm 8, the detector 6 is moved independently of the diaphragm 8, so that the image region 11 is moved as shown in FIG. 3b. The examination can naturally also begin with an image area which is in the center of the detector 6 and said image area can be moved during the examination to the edge or into a corner.

Figure 4A:
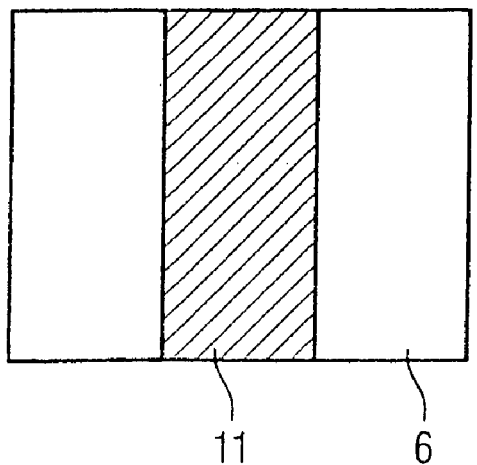
FIGS. 4a and 4b shows a detector whereby the diaphragm is moved during the course of an examination
Figure 4B:
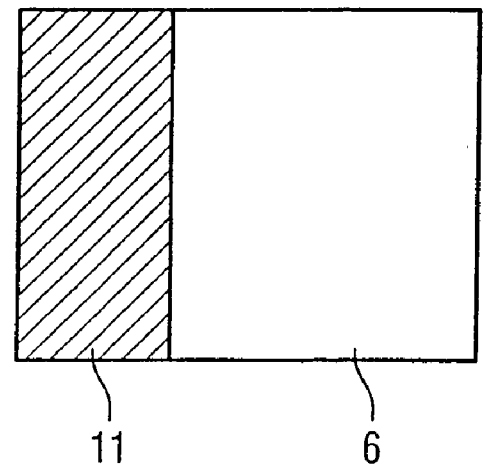

FIGS. 4a and 4b show the detector when the adjustment of the diaphragm is changed over the course of an examination.

With the detector 6 displayed in FIG. 4a, the diaphragm 8 is adjusted such that the image area is located in the center of the detector 6 and is restricted left and right by means of the diaphragm elements 9, 10.

Further into the examination, the diaphragm elements 9, 10 are moved such that the image area 11 is moved into the position displayed in FIG. 4b. The diaphragm elements 9, 10 must not necessarily be moved to the same degree, both diaphragm elements 9, 10 can be moved independently of one another.

The invention claimed is:

1. An X-ray device, comprising:
   an X-ray emitter for emitting X-rays;
   an asymmetrically adjustable diaphragm device in a path of the X-rays for guiding the X-rays to an examination area, wherein the diaphragm device includes a plurality of individually moveable diaphragm aperture elements; and
   an X-ray detector in the path of the X-rays downstream from the examination area, the X-rays limited to a faded-in examination sub-area on the detector by the diaphragm device, and the detector reading only the faded-in examination sub-area, wherein the detector comprises a plurality of a-Si-plates and selectively processes the X-rays detected by each a-Si-plate.

2. The X-ray device according to claim 1, wherein the diaphragm device includes two oppositely arranged pairs of diaphragm aperture elements.

3. The X-ray device according to claim 1, wherein the detector and the faded-in examination sub-area to be processed by the detector are simultaneously movable during a medical X-ray examination.

4. An X-ray device, comprising:
   an X-ray emitter for emitting X-rays;
   an asymmetrically adjustable diaphragm device in a path of the X-rays for guiding the X-rays to an examination area; and
   an X-ray detector in the path of the X-rays downstream from the examination area, the X-rays limited to a faded-in examination sub-area on the detector by the diaphragm device, and the detector reading only the faded-in examination sub-area, wherein the detector comprises a plurality of a-Si-plates sensitive to the X-rays, and selectively processes the X-rays detected by each a-Si-plate.

* * * * *